(12) United States Patent
Daas et al.

(10) Patent No.: US 12,285,164 B2
(45) Date of Patent: Apr. 29, 2025

(54) ANASTOMOSIS DEVICE

(71) Applicant: Lydus Medical Ltd., Raanana (IL)

(72) Inventors: Kamal Daas, Tira (IL); Muhamad Mansur, Tira (IL); Dean Ad-El, Mazor (IL); Jessica Weiss, Tel Aviv (IL); Boaz Harari, Ganey Tikva (IL)

(73) Assignee: LYDUS MEDICAL LTD., Raanana (IL)

( * ) Notice: Subject to any disclaimer, the term of this patent is extended or adjusted under 35 U.S.C. 154(b) by 895 days.

(21) Appl. No.: 17/310,404

(22) PCT Filed: Jan. 29, 2020

(86) PCT No.: PCT/IL2020/050108
§ 371 (c)(1),
(2) Date: Jul. 30, 2021

(87) PCT Pub. No.: WO2020/157753
PCT Pub. Date: Aug. 6, 2020

(65) Prior Publication Data
US 2022/0096078 A1    Mar. 31, 2022

(30) Foreign Application Priority Data
Jan. 31, 2019 (IL) .......................... 264561

(51) Int. Cl.
*A61B 17/062* (2006.01)
*A61B 17/04* (2006.01)
(Continued)

(52) U.S. Cl.
CPC ........ *A61B 17/062* (2013.01); *A61B 17/0469* (2013.01); *A61B 17/11* (2013.01);
(Continued)

(58) Field of Classification Search
CPC .......... A61B 17/062; A61B 2017/1132; A61B 17/0469; A61B 2017/1107; A61B 17/11
See application file for complete search history.

(56) References Cited

U.S. PATENT DOCUMENTS

| 3,265,069 A | 8/1966 | Healey, Jr. et al. |
| 3,316,914 A * | 5/1967 | Collito .................. A61B 17/11 227/19 |

(Continued)

FOREIGN PATENT DOCUMENTS

| CN | 1722989 A | 1/2006 |
| CN | 101612053 A | 12/2009 |

(Continued)

*Primary Examiner* — Darwin P Erezo
*Assistant Examiner* — Christina C Lauer
(74) *Attorney, Agent, or Firm* — Vorys, Sater, Seymour and Pease LLP; Anthony P. Venturino; Maryellen Feehery Hank

(57) ABSTRACT

Provided is an anastomosis arrangement for joining two opposite stumps of a tubular organ in a streamlined anastomosis procedure. The arrangement includes a pair of axially symmetric stump-coupling members that accommodate pairs of counterpart suturing needles, linked together by common suturing threads, and manipulable by a needle-manipulation element to extract the needles tips from the stump-coupling members for piercing walls of the stump.

19 Claims, 12 Drawing Sheets

(51) Int. Cl.
  *A61B 17/11* (2006.01)
  *A61B 17/00* (2006.01)
(52) U.S. Cl.
  CPC .............. *A61B 2017/00876* (2013.01); *A61B 2017/0472* (2013.01); *A61B 2017/1107* (2013.01); *A61B 2017/1132* (2013.01)

(56) References Cited

U.S. PATENT DOCUMENTS

| | | | |
|---|---|---|---|
| 4,553,543 A * | 11/1985 | Amarasinghe | A61B 17/11 606/153 |
| 4,744,362 A | 5/1988 | Gruendler | |
| 5,330,503 A | 7/1994 | Yoon | |
| 5,417,699 A | 5/1995 | Klein et al. | |
| 5,554,162 A * | 9/1996 | DeLange | A61B 17/0469 606/153 |
| 5,746,757 A | 5/1998 | McGuire | |
| 6,042,583 A * | 3/2000 | Thompson | A61F 2/0031 606/232 |
| 6,190,396 B1 | 2/2001 | Whitin et al. | |
| 6,461,367 B1 | 10/2002 | Kirsch et al. | |
| 10,182,812 B1 | 1/2019 | Ashraf | |
| 2002/0029989 A1 * | 3/2002 | Anthony | A61B 50/362 206/366 |
| 2002/0193809 A1 | 12/2002 | Meade et al. | |
| 2003/0032968 A1 | 2/2003 | Kirsch et al. | |
| 2004/0199185 A1 | 10/2004 | Davignon | |
| 2005/0171563 A1 | 8/2005 | Heinrich et al. | |
| 2005/0288697 A1 | 12/2005 | Tei et al. | |
| 2006/0167485 A1 | 7/2006 | Blatter | |
| 2008/0275472 A1 | 11/2008 | Yossepowitch et al. | |
| 2009/0312775 A1 | 12/2009 | Gilkey et al. | |
| 2011/0028998 A1 | 2/2011 | Adams et al. | |
| 2013/0096581 A1 | 4/2013 | Gilkey et al. | |
| 2014/0276975 A1 | 9/2014 | Argentine | |
| 2015/0351744 A1 | 12/2015 | Deck et al. | |
| 2018/0199943 A1 | 7/2018 | Daas et al. | |
| 2018/0242967 A1 | 8/2018 | Meade | |
| 2019/0150928 A1 * | 5/2019 | Boiman | A61B 17/0482 |

FOREIGN PATENT DOCUMENTS

| | | |
|---|---|---|
| CN | 102076344 A | 5/2011 |
| CN | 102245114 A | 11/2011 |
| CN | 102292033 A | 12/2011 |
| CN | 102548488 A | 7/2012 |
| CN | 106535780 A | 3/2017 |
| CN | 107072658 A | 8/2017 |
| CN | 107683115 A | 2/2018 |
| CN | 108348228 A | 7/2018 |
| WO | 2004/000136 A2 | 12/2003 |
| WO | 2005-000127 A1 | 1/2005 |
| WO | 2016/128961 A2 | 8/2016 |

* cited by examiner

ANASTOMOSIS DEVICE

TECHNOLOGICAL FIELD

The present disclosure concerns an assembly and device for use in anastomosis of tubular organs within the body, particularly small tubular organs (such as blood vessels, bile duct, lymph duct, nerve ducts, epididymis, etc.).

BACKGROUND ART

References considered to be relevant as background to the presently disclosed subject matter are listed below:
WO 2016/128961
U.S. Pat. No. 4,744,362
US 2006/0167485
US 2004/0199185
U.S. Pat. No. 5,330,503
US 2005/0288697
U.S. Pat. No. 5,746,757
U.S. Pat. No. 5,417,699
U.S. Pat. No. 3,265,069

Acknowledgement of the above references herein is not to be inferred as meaning that these are in any way relevant to the patentability of the presently disclosed subject matter.

BACKGROUND

Various techniques are known in medical practice for the anastomosis of severed tubular organs, including blood vessels and others. WO 2016/128961 discloses, among others, anastomosis devices for the coupling of two tubular organs, that make use of multiple threads each thread having needles at its two ends, and devices that streamline the suturing procedure intended to join the two vessel portions to one another.
General Description This disclosure provides anastomosis arrangement (namely, one or a combination of two or more parts or elements that are to be used jointly in an anastomosis procedure) for joining two opposite stumps of a tubular organ. The two stumps may be stumps of tubular organs, such as blood vessels or lymph vessels, e.g. cut during surgery or by accident, a stump of a grafted vessel to a vessel at a donor site, etc.

In an anastomosis procedure, a plurality of sutures need to be made between the opposite stumps. In the case of small vessels this may be a complex and time consuming procedure. The arrangement of this disclosure aims to streamline this procedure. The arrangement comprises a pair of axially symmetric stump-coupling members, which may be separate or joined to one another through an integral, axial connecting body or an auxiliary unit holding the coupling members' pair together, that have opposite axial stump-coupling projections that are configured for coupling with the stump by pulling the wall of the stump over the external surface of these projections. Pairs of counterpart (and oppositely oriented) suturing needles, linked together by a common suturing thread, are part of the arrangement and fitted within the coupling members with their tips being accommodated within needle-receiving channels. By axial displacement of a needle-manipulation element, associated with the stump-coupling member, typically in the form of a sleeve fitted over the external surface of the stump-coupling member, the needles tips are extracted to pierce walls of the stumps fitted over the external surface of the stump-coupling projections.

In the following description the term suturing unit will be used to denote a pair of needles that are linked together by a suturing thread; and the term set of needles will be used to denote all the suturing needles that are associated with one stump-coupling member.

One suturing needle of a suturing unit is associated with one of the stump-coupling members and, thus, forming part of one set of needles that are intended for piercing through walls of one of the stumps to be joined together in the procedure; while its counterpart is associated with the other stump-coupling member, forming part of the other set of needles intended for piercing through walls of the opposite stump. All needles of one set of needles are manipulated together in the manner to be explained and, as a result, in a relatively simple process, one set of needles is made to pierce through one stump and the other set made to pierce the other stump. After the needle's tip pierces the stump, each needle may be pulled to thereby pass entirely through the walls of the stump and subsequently pull the suturing thread (linking the needle to the counterpart needle) through the stump walls. In this manner the two stumps become linked by a plurality of suturing threads that can then, after pulling of the stumps away from the stump-coupling members, be proximated to one another and sutured.

As will be explained also further below, the manipulation of the suturing needles from their initial state (in which their tips are accommodated within the stump-coupling members) into a piercing state (in which their tips are biased to pierce through the walls of the stumps laid over the external surface of the stump-coupling members) is by pivoting the needles, that are typically curved, about a pivot point located within the stump-coupling member.

The stump-coupling members and the arrangement may be formed with different dimensions to suit different anastomosis procedures. For example, the stump-coupling members may have different diameters or different geometries to suit different stump dimeters or different anastomosis procedures.

Provided by one embodiment of this disclosure is an anastomosis arrangement for joining two stumps of a tubular organ, that comprises a coupling assembly and suturing units incorporated within the coupling assembly. The coupling assembly comprises a pair of axially-symmetric stump-coupling members that define two opposite axially-extending stump-coupling projections, each of which being configured for coupling with one of the stumps by pulling walls of the stump over external surface thereof to a suturing state. In the suturing state the stump walls cover a stump-engaging portion of said stump-coupling projection.

Each of the stump-coupling members has a set of open channels arranged in an axially-symmetric manner about a longitudinal axis of the stump-coupling member. Each of the channels (i) extends between a rear channel end in said stump-coupling member and a front channel end in the stump-engaging portion of the projection to define a channel axis, (ii) is defined between side walls and a bottom wall that is configured with a pivot point in a mid-channel portion to define a front channel portion and a rear channel portion, and (iii) has a counterpart in the opposite set of channels (formed in the opposite stump-coupling member) that extends along the same channel axis in an opposite direction to the opposite stump-coupling portion. Each of the channels in one of the stump-coupling members has a counterpart in the other of said members.

Each of said stump-coupling members has an needle manipulation element that is axially displaceable between a front position nearer said stump-coupling projection and a rear, needle extraction position.

Each of the suturing units comprises a suturing thread and two curved suturing needles, each needle with a tipped front and a thread-coupled rear that is coupled to the thread. Each of the suturing needles is accommodated in one of the channels, with one of the suturing needles of each unit being accommodated in a channel of one of said stump-coupling members and the other suturing needle of the unit in the counterpart channel in the other of said stump-coupling members. The front end of each needle is fully accommodated within the channel proximal to the front channel end, with a mid-portion of the needle resting against said pivot point and the rear end of the needle extending out of the channel proximal the rear channel end. A rear end of the needle is coupled to the needle manipulation element of the respective stump-coupling member, such that upon the axial displacement thereof into the needle extraction position, the needles pivot about said pivot point, whereby their tipped front is pivotally displaced out of said front channel end to pierce through the stump walls when in said suturing state.

By one embodiment, the two stump-coupling members are connected to one another through a central connecting body and, thus, integral with one another to form a unitary anastomosis device. By another embodiment, the two stump-coupling members are separately formed and are held together by an auxiliary unit, e.g. a bracket, frame, jig, bridge, etc. that maintains integrity and typically holds the stump-coupling members in a co-axial configuration. The auxiliary unit may also be part of an actuation device configured for displacing the needle manipulation elements.

The needles manipulation element may be formed as a sleeve or an annular body fitted over a portion of the stump-coupling member's exterior and axially slidable along and rotatable over the external surface of the stump-coupling member. Said needles manipulation element is configured for engaging the rear end of the suturing needle, for example by means of openings in said element through which the needle's rear end protrudes. Such openings may be formed to have a general L-shape, one arm of the L-shaped opening extending from a distal edge of the needles manipulation element, whereby the rear end of the needles may be captured within said openings by push-and-turn manipulation of said element.

The coupling assembly has, typically, a mirror symmetry about a plane of symmetry in between the two coupling members, e.g. in a mid-portion of the central body integrating the two stump-coupling members into one device.

The stump-coupling projection may have a variety of geometries to fit different uses. It has typically a circular cross-section throughout at least distal portions thereof that couple with the tubular organ's stump, although other cross-sections (e.g. hexagonal, heptagonal, octagonal, nonagonal, decagonal, etc.) may also be possible. It may be generally cylindrical, conical or frustum-conical. In order to ease or streamline the coupling with the stump, the distal end of the stump-coupling member may be tapered.

Each of the front and rear channel portions has, typically, a curvature that matches that of the suturing needle. The axial displacement of the needles manipulation element into the needle extraction position causes the suturing needles to pivot about the pivot point between a first resting state, in which a portion of the needle forward said mid-portion rests against the front channel portion, and a second resting state in which a portion of the needle rearward said mid-portion rests against the rear channel portion. The curvature of each of the rear channel portion and front channel portion may be arched about, respective, rear curvature center and front curvature center, the rear curvature center being rearward offset vis-à-vis the front curvature center.

The suturing needles may, each, have a tip that is angled with respect to the trajectory defined by the needle's curvature, e.g. in a general inward radial direction.

The anastomosis assembly typically comprises a retaining element for retaining the suturing needles within the channels. This retaining element may be integrally formed with the stump-coupling member or may be a separate element fitted over the open channels, e.g. an elastic ring accommodated in a circumferential groove that may be formed at the rear end of the stump-coupling member.

Also provided by this disclosure is a coupling assembly for use in anastomosis arrangement as described above.

By an embodiment, the coupling assembly comprises a pair axially-symmetric stump-coupling members defining two opposite axially-extending stump-coupling projections, each of said projections being configured for coupling with one of the stumps by pulling walls the stump over external surface thereof to a suturing state in which the stump walls cover a stump-engaging portion thereof; two opposite sets of open channels arranged in an axially-symmetric manner about the axis, each of the channels (i) extending between a rear channel end in said stump-coupling member and a front channel end in the stump-engaging portion of the projection to define a channel axis, (ii) being defined between side walls and a bottom wall that is configured with a pivot point in a mid-channel portion to define a front channel portion and a rear channel portion, (iii) having a counterpart in the opposite set that extends along the same channel axis in an opposite direction to the opposite stump-coupling portion, and (iv) the channels being each configured for receiving and accommodating a suturing needle, each needle having a tipped front and a thread-coupled rear that is coupled to the thread, such that, when received within the channel, a front end of each needle being fully accommodated within the channel proximal to a front channel end, a mid-portion of the needle resting against said pivot point and the rear end of the needle extending out of the channel proximal a rear channel end; and two needles manipulation elements, one in each stump-coupling member, each being axially displaceable between a front position nearer said stump-coupling projection and a rear, needle extraction position.

An actuator device for operating the arrangement is also an aspect of this disclosure. The actuator device may comprise a handle and two arms each configured for coupling at a distal portion to one of the needles manipulation elements; and an actuator configured for displacing the arms to cause each of the distal portions to move towards the other to thereby axially displace the needles manipulation elements into a needle extraction position.

The actuator device may, by an embodiment, comprise two holding members, each for holding one stump-coupling member in a pair of separate stump-coupling members in a releasable manner.

By an embodiment, the actuator device comprises a thread-holder for releasable association with the suturing threads, e.g. about or at a mid-position of the suturing thread. The thread-holder may be designed to maintain tension in the threads while associated with the thread-holder.

The actuator device may comprise a selector permitting selected displacement of one of the arms, and hence one of the needles manipulation elements. Each of the two arms may have a coupling end that fits into a groove formed on the needles manipulation element's external face.

Once the needles are made to pierce through the stump walls, the needles' tips need to be gripped so that the needles can be pulled through the walls, pulling the suturing thread after them. For this purpose the surgeon needs to have access to all needles' tips. Some of the needles pierce wall portions that are in a side of the stump opposite that facing the surgeon and accessing tips of such needles may be difficult. In order to overcome this difficulty, the actuator device may comprise a revolving arrangement for revolving the arrangement about the axis. Once so revolved, the arrangement causes the coupled stumps to revolve with it, bringing the stump's opposite side to face the surgeon; whereupon the surgeon can easily access the respective tips and pull the needles through the stump walls.

Provided by this disclosure is also an actuator device for operating an anastomosis assembly that is configured for guiding or manipulating needles of a suturing unit in an anastomosis procedure. The suturing unit comprises two needles at opposite ends of a suturing thread. In the anastomosis procedure, opposite needles of the suturing unit pierce and pass through to cause the suturing thread to engage walls of opposite stumps. The device uniquely comprises at least one magnetic element for magnetically holding the needles after passing through the stump wall. The magnetic element may also be included in any of the actuator devices described in previous paragraphs.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 3B-3C correspond, respectively, to the states of FIGS. 1A-1B and FIGS. 2A-2B.

FIGS. 4A-4C shows an anastomosis arrangement of another embodiment of this disclosure, coupled to an actuator device for operating the anastomosis arrangement in an anastomosis procedure, wherein FIG. 4A is an overview perspective view, FIG. 4B shows an enlarged view of the distal portion of the actuation device with the anastomosis arrangement associated thereto, and FIG. 4C shows a longitudinal cross-section and perspective view of said distal portion.

DETAILED DESCRIPTION OF EMBODIMENTS

In the following description the invention will be illustrated with reference to three embodiments, one illustrated in FIGS. 1A-3C, another in FIGS. 4A-4C, and yet another in FIGS. 5A-5E. As can be appreciated, these embodiments are meant to illustrate the general principles of the arrangement, assembly and devices disclosed herein and is not limited to the specifics of these embodiments. When discussing some of the elements, some potential modifications may be mentioned. However, modifications may also be possible, as appreciated by a person of skill in the art, also in elements in connection with which modifications are not specifically discussed herein, all within the general teachings of this disclosure.

Figure 1A:
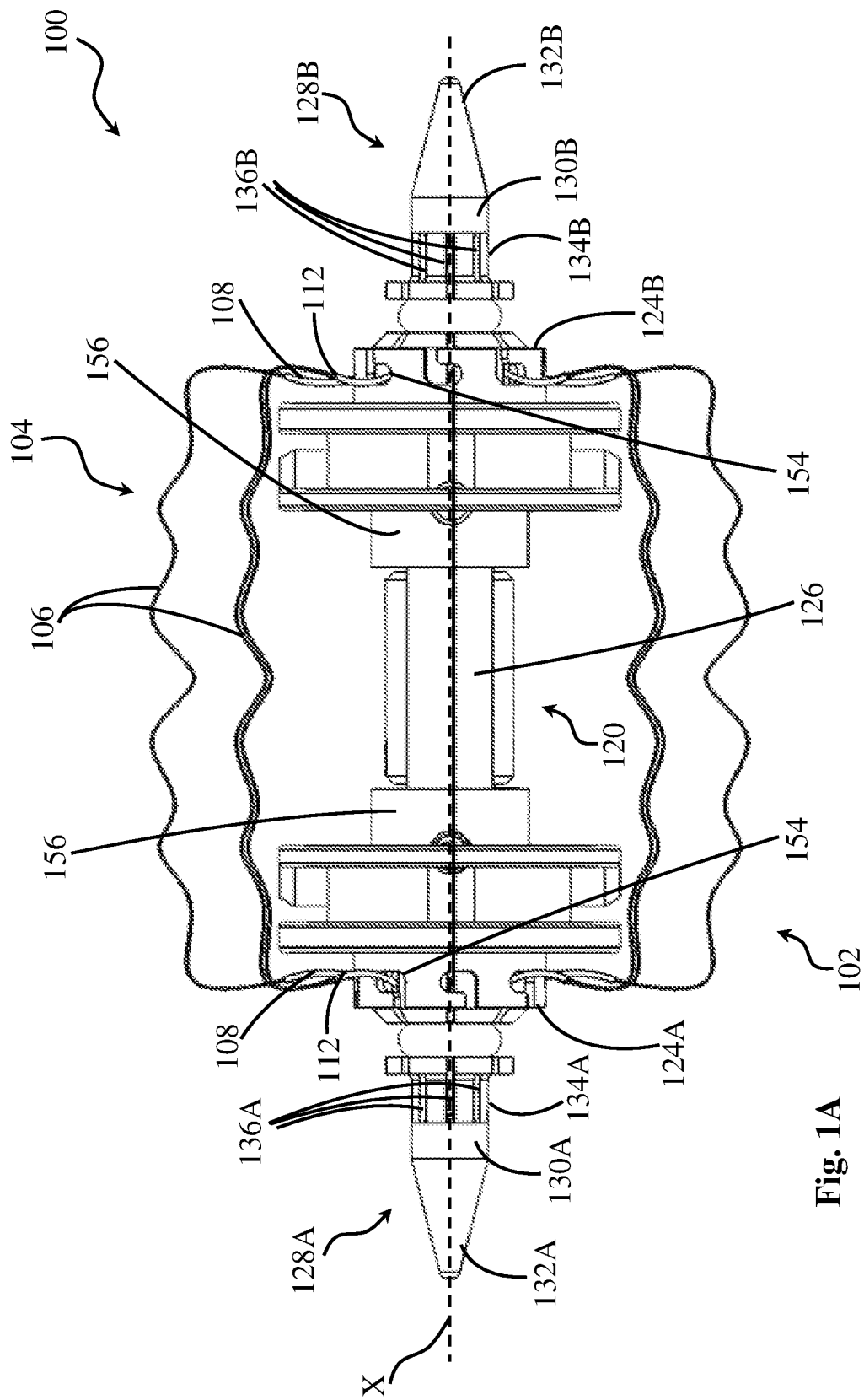
FIGS. 1A and 1B are, respectively, side view of and a longitudinal cross-section through an anastomosis arrangement according to an embodiment of this disclosure, in which the coupling assemblies are connected to one another through a central connecting body, in a deployment state.
Figure 1B:
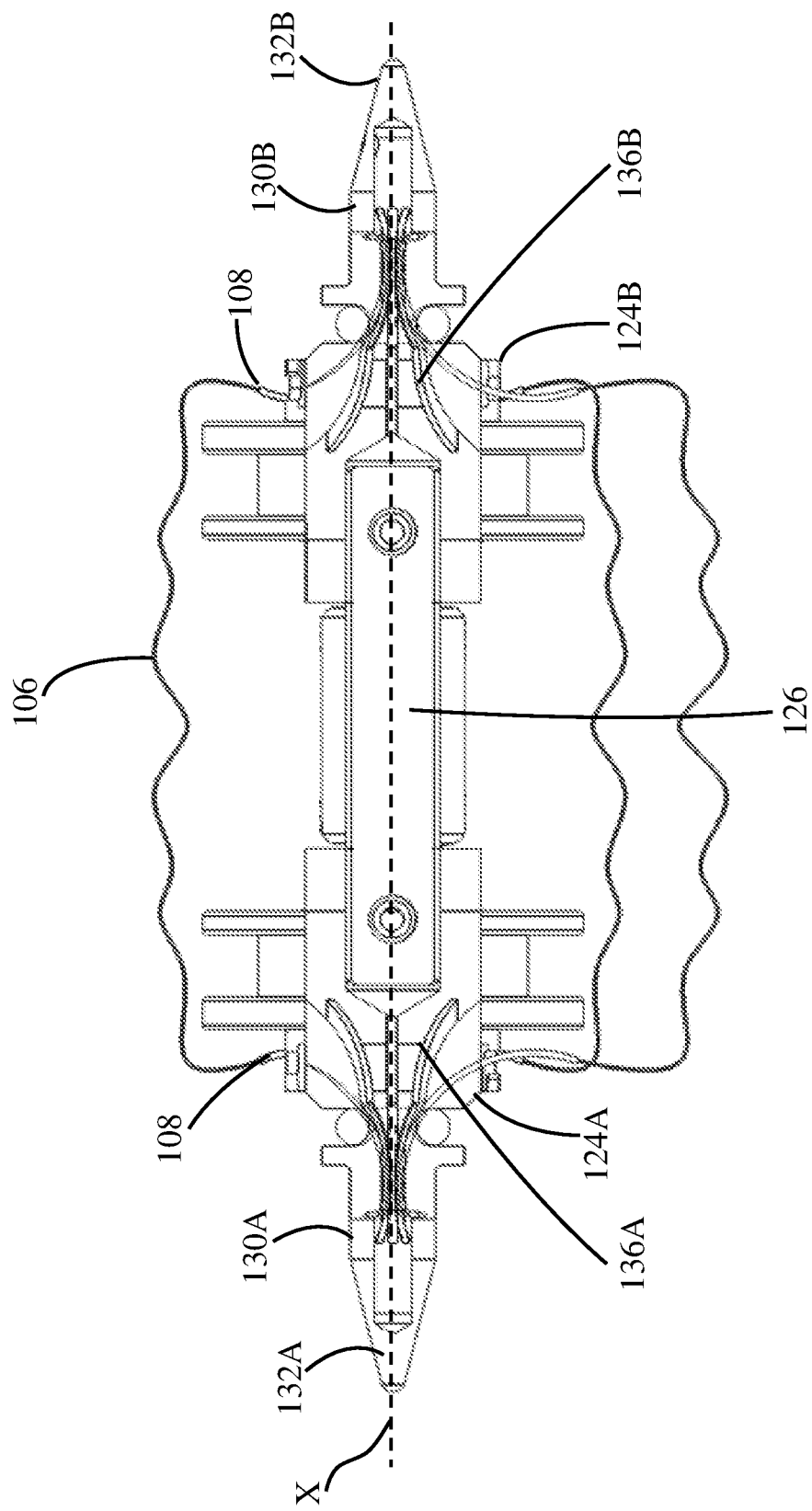
Figure 2A:
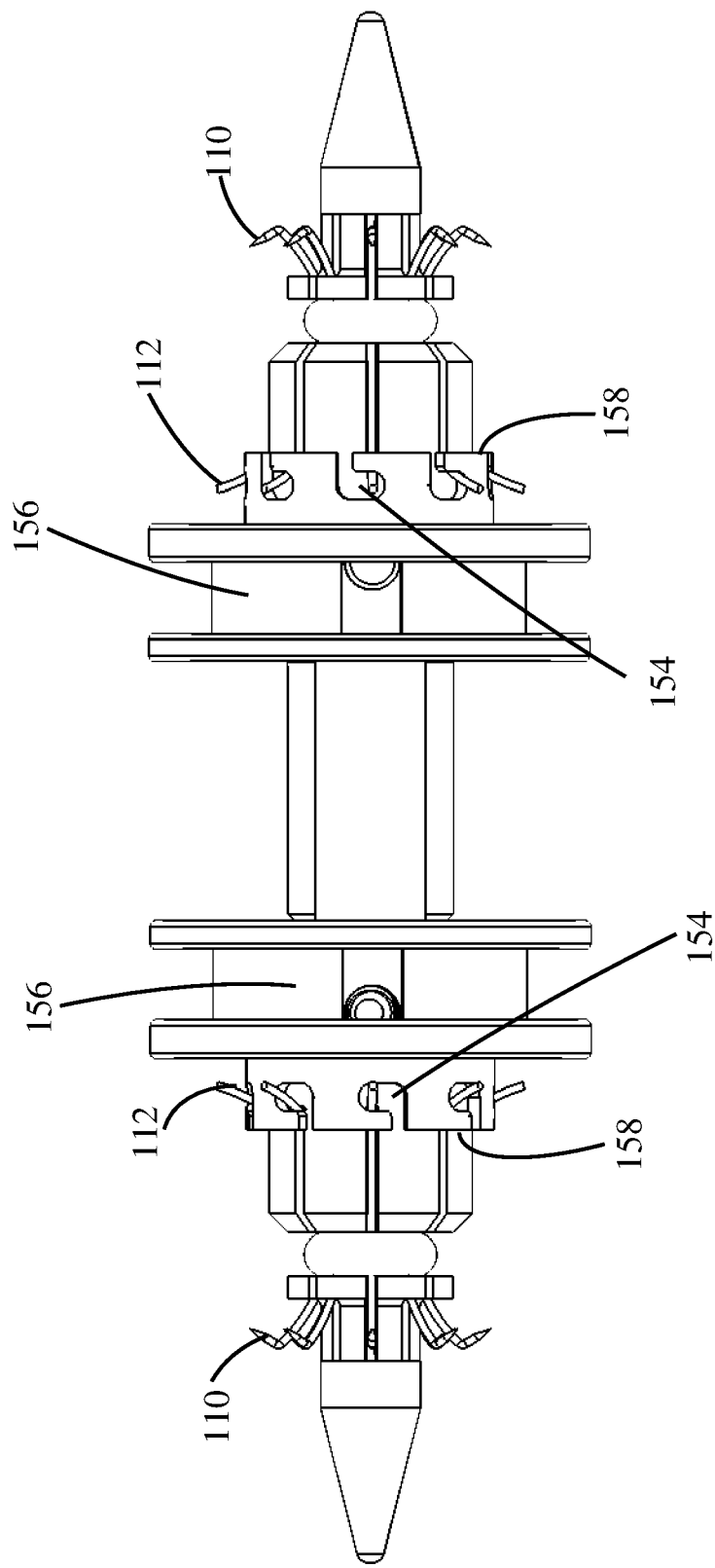
FIGS. 2A and 2B are, respectively, side view of and a longitudinal cross-section through the anastomosis arrangement of FIGS. 1A-1B in a suturing state.
Figure 2B:
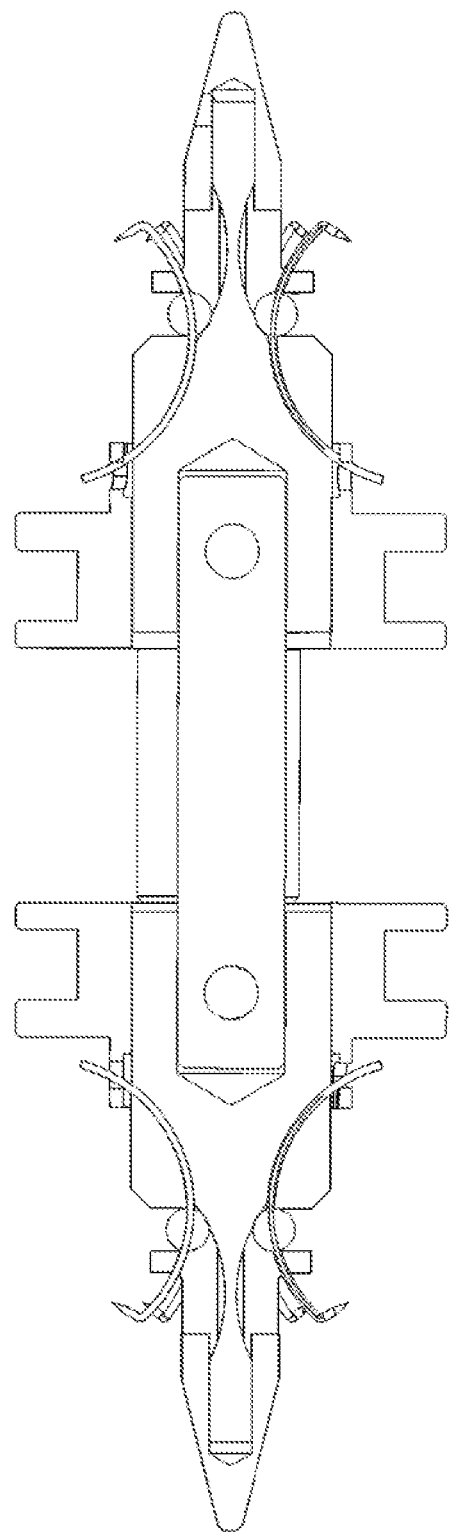

Reference is first being made to FIGS. 1A-2B, showing the anastomosis arrangement in which the stump-coupling members are integrated with a central connecting body. FIGS. 1A-1B show the arrangement in the initial, deployment state, while FIGS. 2A-2B show the device in with the arrangement is in its piercing state.

The arrangement 100 comprises a coupling assembly 102 and a plurality of suturing units 104, each comprising a suturing thread 106 and two curved suturing needles 108, each needle having a tipped front end 110 (can best be seen in FIGS. 2A-2B) and a rear end 112 coupled to the suturing thread 106. It is to be noted that in FIGS. 2A-2B the suturing threads have been omitted for ease of viewing. The coupling assembly 102 has a central connecting body 120 that is axially symmetric about an axis X and extends between two opposite body ends 124A, 124B at the opposite sides of a mid-portion 126 of the central connecting body 120. Integral with and axially extending from the central connecting body are two opposite axially-extending stump-coupling members 128A, 128B, each of which has a generally circular cross-section with a generally cylindrical axially-extending stump-coupling projection 130A, 130B having a tapered distal end 132A, 132B, thus having a general frustum-conical shape. Each of the stump-coupling projections is configured, through its shape, for coupling with one of the stumps that is intended to be joined together during the anastomosis procedure by pulling walls of the stumps (not shown) over the external surface of the projection up to a suturing state, in which the stump walls cover a stump-engaging portion 134A, 134B of the projections 130A, 130B, respectively.

As can be seen, the central connecting body 120 is mirror symmetric about a plane at and normal to the mid-portion of the body. It is to be noted, however, that this is but an example and where, for example, the assembly is intended for joining together two stumps that have a different diameter, the body being configured for coupling with a stump of a relatively larger diameter at one of its ends and for coupling with a narrower stump at its other end.

Two sets 136A, 136B of open channels are formed in the projections, the two sets being arranged in an axially-symmetric manner about the axis X. Each of the channels 136, best seen in FIG. 3A, extends between a rear channel end 140 in the stump-coupling member 128 and a front channel end 142 in the stump-engaging portion 134, defining a channel axis; the channel 136 having a counterpart at the opposite end of body 120 (not shown) extending along the same channel axis. Each channel is defined between sidewalls, one of which 144 is seen in the cross-sectional view of FIG. 3A and a bottom wall 146 with a pivot point 148 defined in a mid-channel portion. In this specific embodiment, pivot point 148 divides the channel to a front channel portion 150 and a rear channel portion 152, each of which having a curvature that matches that of the suturing needle, as can be seen in FIGS. 3B and 3C.

Each rear end 112 of the needles 108 engages in opening 154 formed at a front end of a needles manipulation element 156, as can best be seen in FIGS. 1A and 2A. Opening 154 has a general L-shape, one arm of which extends from the distal edge 158 of element 156, permitting the capture of the needles within said openings by push-and-turn manipulation of the element. Manipulation elements 156 are fitted onto the central body, one at each body end, and each being inwardly axially displaceable from its initial position seen in FIGS. 1A-1B towards a mid-body portion to the position shown in FIGS. 2A-2B.

Figure 3A:
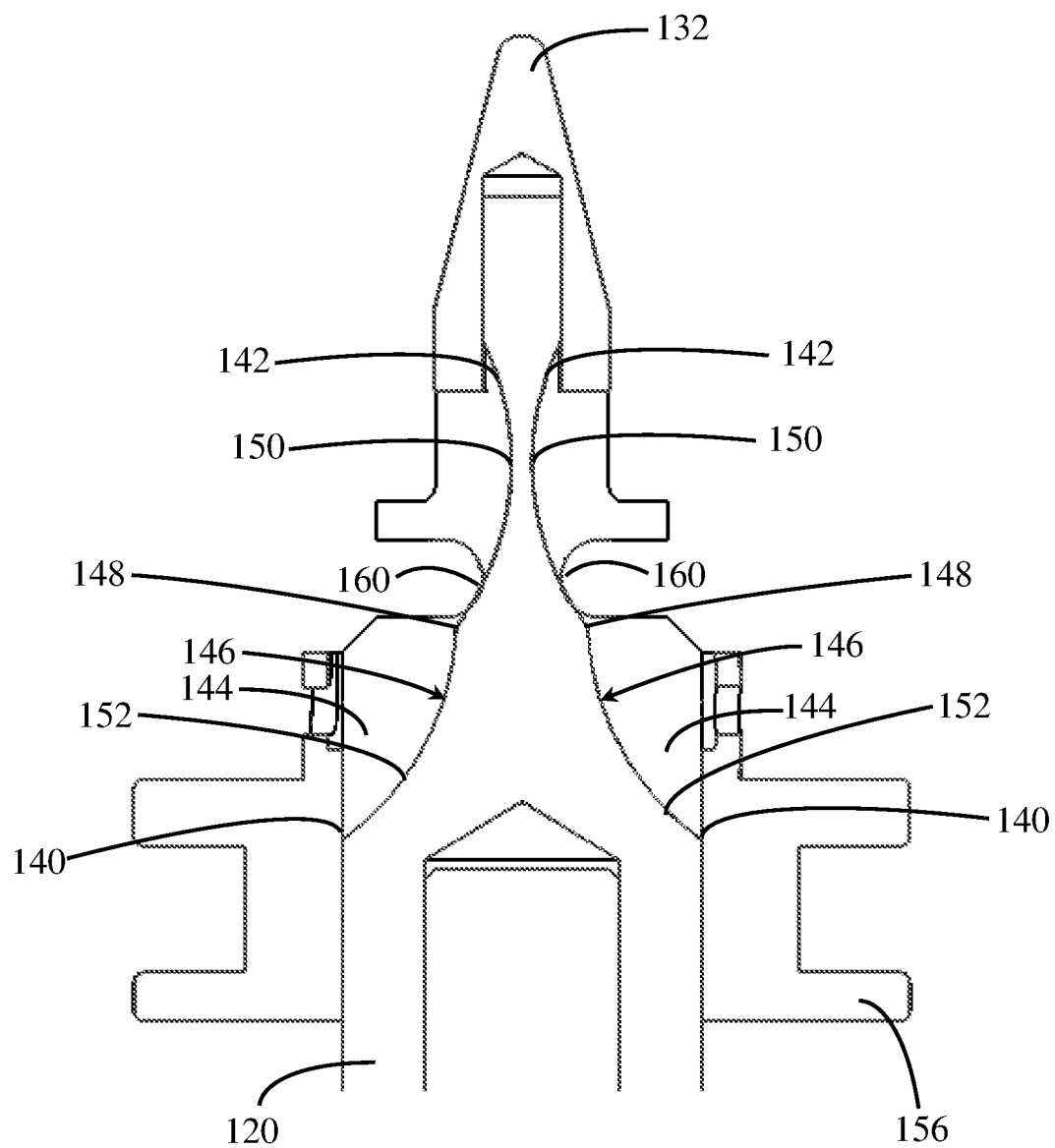
FIGS. 3A-3C are schematic longitudinal cross-sections of one end of the central connecting body and through the open channels, illustrating the body without suturing needles within the channels (FIG. 3A), with the needles in the channels in a deployment position (FIG. 3B) and in a suturing position (FIG. 3C)
Figure 3B:
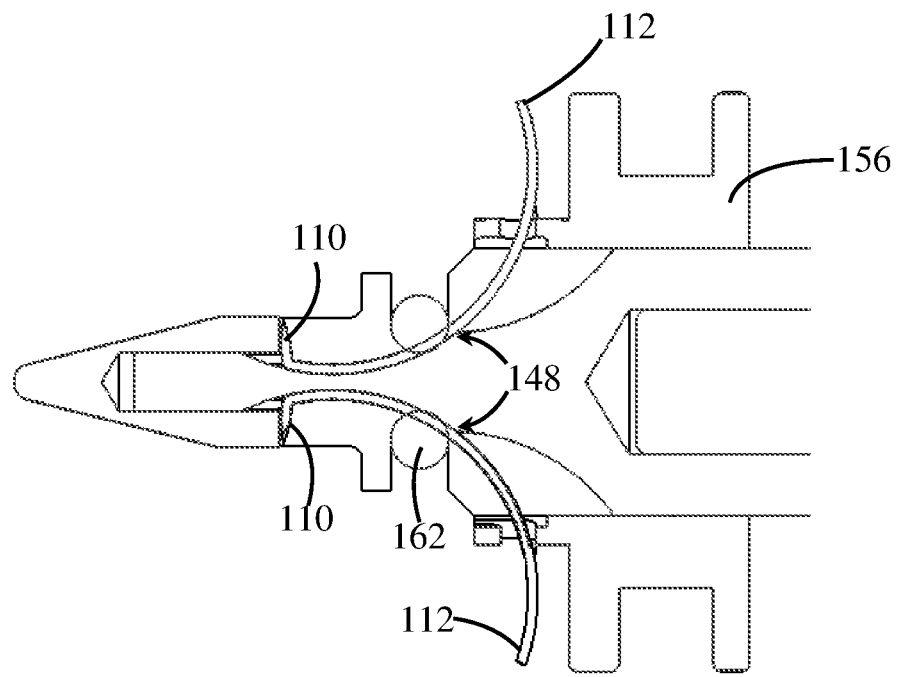
Figure 3C:
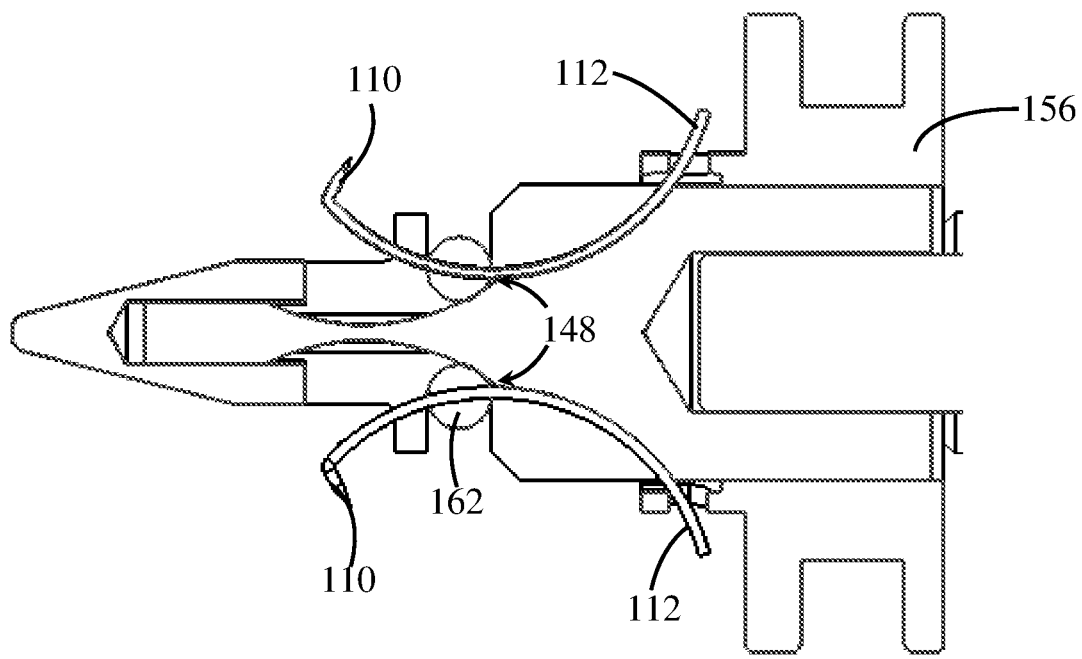

FIG. 3B shows the suturing needles 108 accommodated, each, within a channel 138 with the needle front portion being fully accommodated within the channel, resting against the bottom wall of the front channel portion 150. The tipped front end 110 of the suturing needle 108 is angled with respect to the trajectory defined by the needle's curvature. By one example, shown in FIGS. 3B-3C, the tip of the needle points in a general inward radial direction. However, the needle tip, as can be appreciated, can also have some other configurations and is not limited to such angled or radial direction.

The curvature of the bottom wall of the front portion and also that of the rear portion of the channel, and hence also that of the needle, is typically circular, namely being arched and tracing a section of an imaginary curvature (e.g. circle) defined about a curvature center (not shown), the bottom wall of the channel's front portion being arched about an imaginary front curvature center and the rear portion of the channel being arched about an imaginary rear curvature center, the rear curvature center being rearward offset vis-à-vis the front curvature center. It should be pointed out that an arched bottom wall tracing a section of an imaginary circle is but an example, and the curvature may have other trajectories, e.g. hyperbolic, parabolic, etc.

As can be seen in FIG. 3B, in the initial or deployment state, the needle's front portion rests against the bottom wall of the channel's front portion 150 and the needle tip 110 is fully accommodated within the channel. A mid-portion of the needle rests against the pivot point 148, and once the needles manipulation element 156 is inwardly axially displaced from its initial, distal, position seen in FIGS. 1A-1B and 3B, towards the mid-body portion, into the state seen in FIGS. 2A-2B and FIG. 3C, the needle pivots about the pivot point 148, whereupon its rear portion 112 comes to rest against the bottom wall of the channel rear portion 152. Once so pivoted, tip 110 shifts into a piercing position, in which it can pierce walls of the stump (not shown) laid over the stump-engaging portion 134. The needles can then be pulled through the stump walls, e.g. by the use of forceps, pulling the suturing thread with them and, after removal of the coupling device 102, the two stumps can be sutured one to the other.

Formed at a rear end of stump-coupling member 128 is an annular groove 160 accommodating an elastic O-ring 162. This elastic O-ring functions to retain the needles within the open channels 138 and in particular ensures that the needles are retained within the channels during their pivoting movement from their resting state and the deployment position seen in FIG. 3B to the piercing state seen in FIG. 3C. Once the needles and the suturing threads have been pulled through the stump walls, this elastic O-ring may be removed, e.g. by cutting or severing.

The needles manipulation elements may be axially displaced by direct manipulation, e.g. by the use of forceps. However, in accordance with an embodiment of this disclosure shown in FIGS. 4A-4C, such displacement may be achieved by the use of an actuator device. In the embodiment of FIGS. 4A and 4B like elements to those of the previously described embodiment will be given like reference numerals, shifted by 100, for example, needle manipulation element 256 in FIGS. 4A-4C, serves the same functions element 156 in FIGS. 1A-3C. The reader is referred to the description of FIGS. 1A-3C for explanation of any element illustrated but not specifically described below.

Figure 4A:
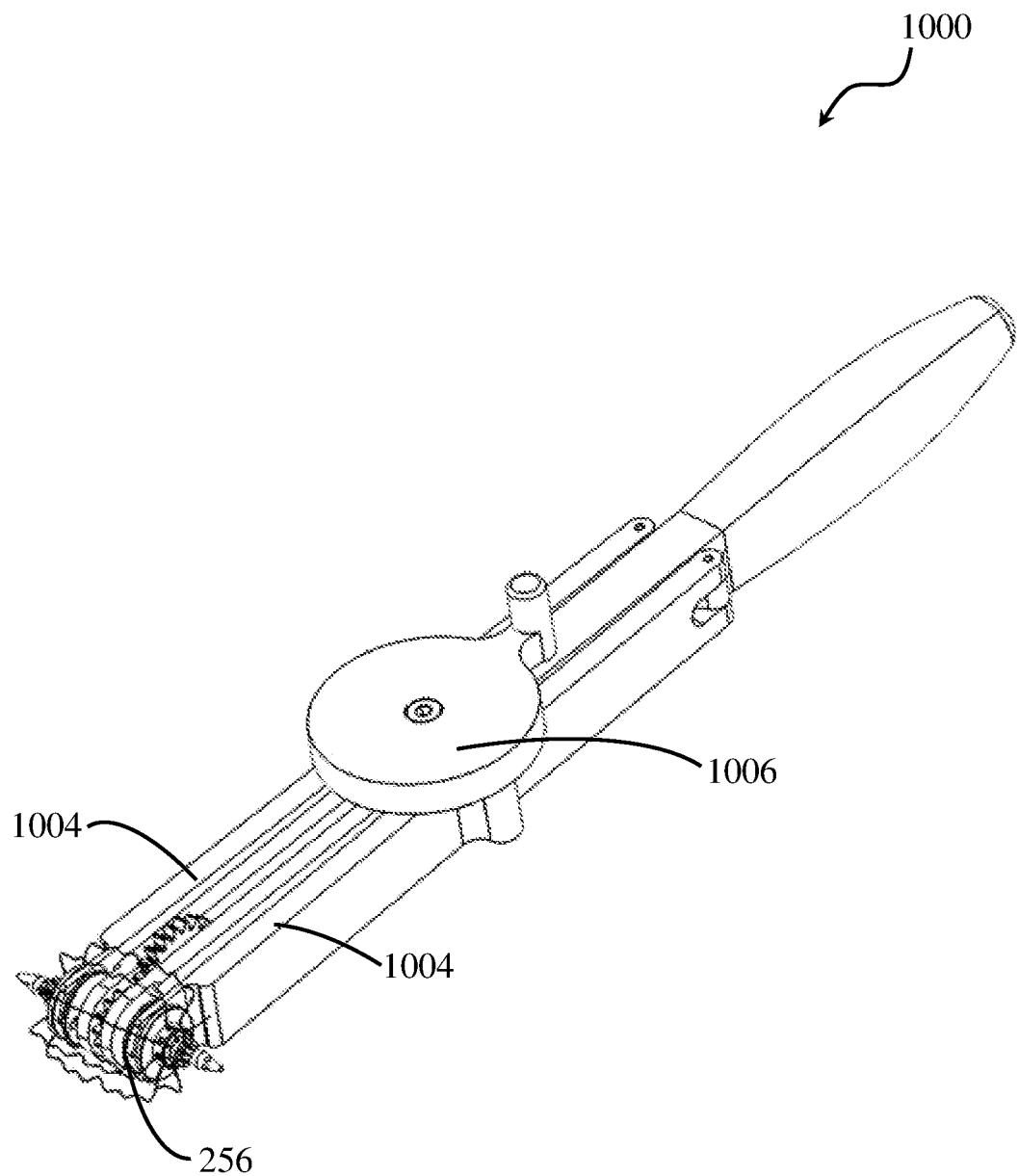
Figure 4B:
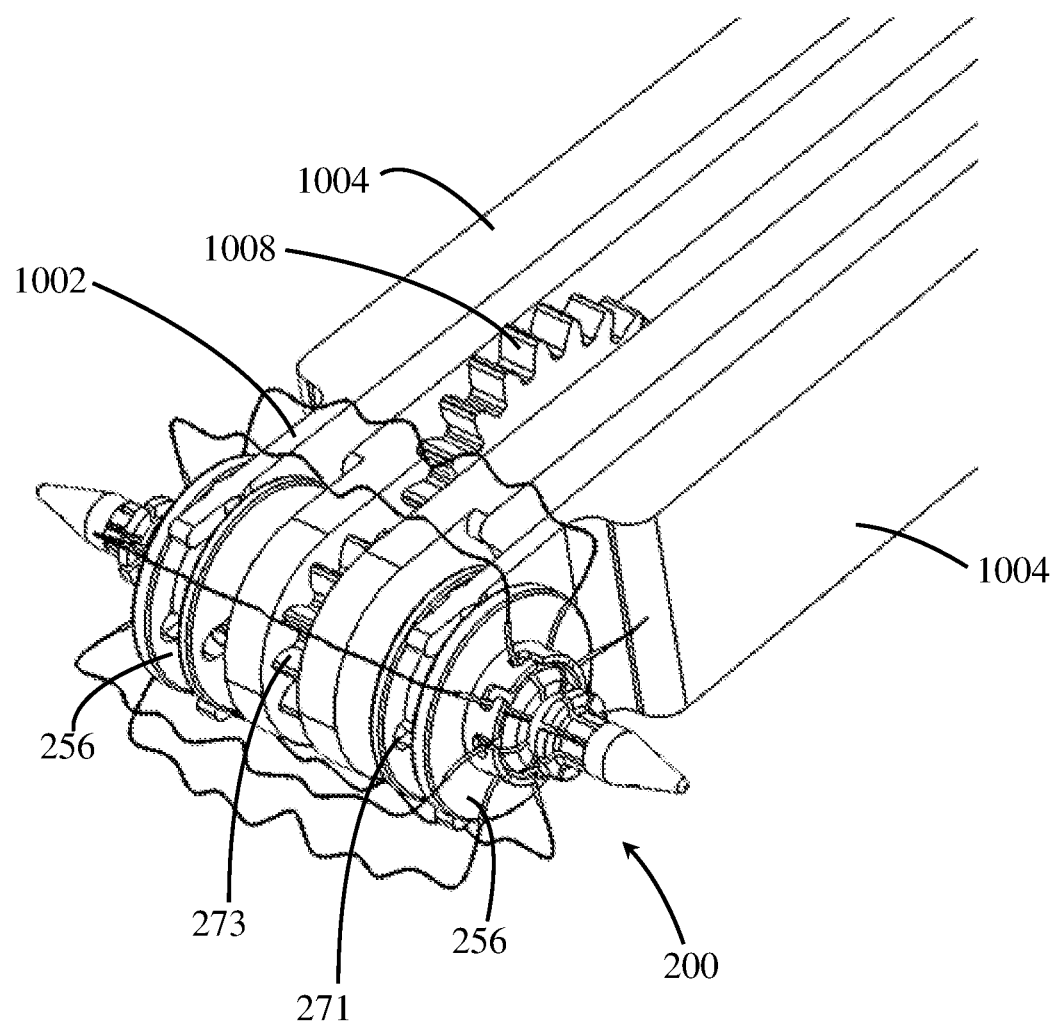
Figure 4C:
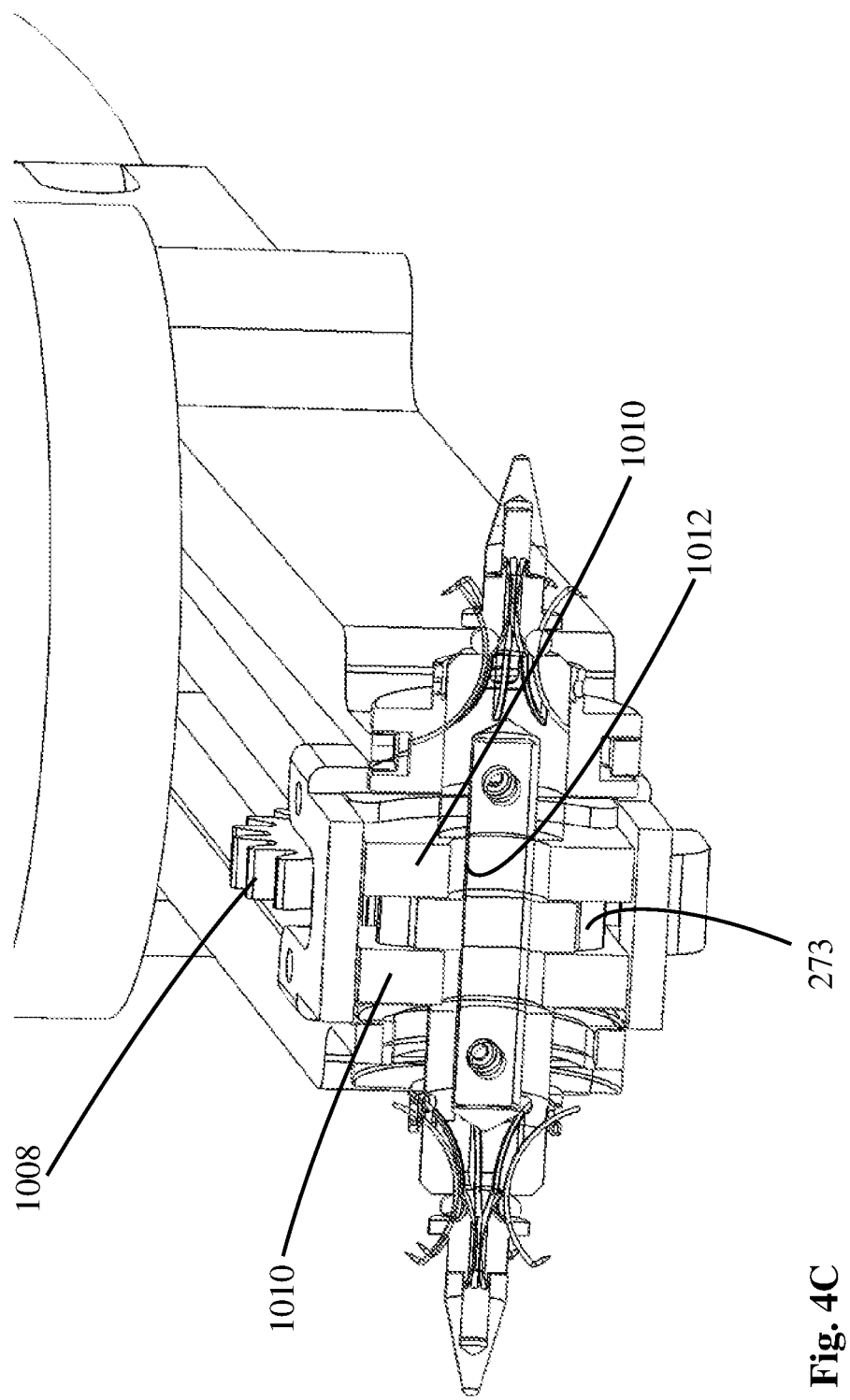

The actuator device 1000 illustrated in FIGS. 4A-4C may serve two independent functions: one is to manipulate the needles manipulation elements 256 and the other to rotate the entire arrangement about its axis to enable access to tips of needles that are in a side opposite that facing the surgeon (i.e. hidden side) to permit their gripping for the purpose of pulling them through the stumps' walls.

In this specific example, needles manipulation element 256 has an annular external recess 271 that is configured for engagement with an end portion 1002 of arm 1004 of actuator device 1000. Arms 1004 are configured for inward axial displacement, to thereby inwardly axially displace the needles manipulation elements 256 towards the mid-portion of body 226. This may be achieved by means of an actuation element 1006 that, by some embodiments, permits selectable inward displacement of only one or both of the arms. As can further be seen in FIGS. 4A-4C, the mid-portion of the body 226 is configured with an integral cogwheel 273 that is coupled to a cogwheel 1008 of actuator device 1000. The body 226 is securely coupled with the actuator device 1000 through bored extensions 1010 with axial bores 1012 that accommodate sections of the body's mid-portion between cogwheel 273 and needles manipulation element 256.

Once all needles are in the state seen in FIG. 4C, in which their tips pierce through the stumps' walls, the surgeon can first grip and pull needles at the surgeon-facing side, and then cogwheel 1008 may be turned to cause the entire assembly 200 to rotate about the axis and bring the needles tips from the hidden side to the front, permitting their gripping and pulling in the same manner.

By another embodiment, shown in FIGS. 5A-5E, the anastomosis arrangement 300 comprises two separate coupling assemblies 302, each coupled to an actuator device 3000. In the embodiment of FIGS. 5A-5E like elements to those described in connection with FIGS. 1A-3C will be given like reference numerals, shifted by 200, for example, needle manipulation element 356 in FIGS. 5A-5E, serves the same functions element 156 in FIGS. 1A-3C. The reader is referred to the description of FIGS. 1A-3C for explanation of any element illustrated but not specifically described below.

Figure 5A:
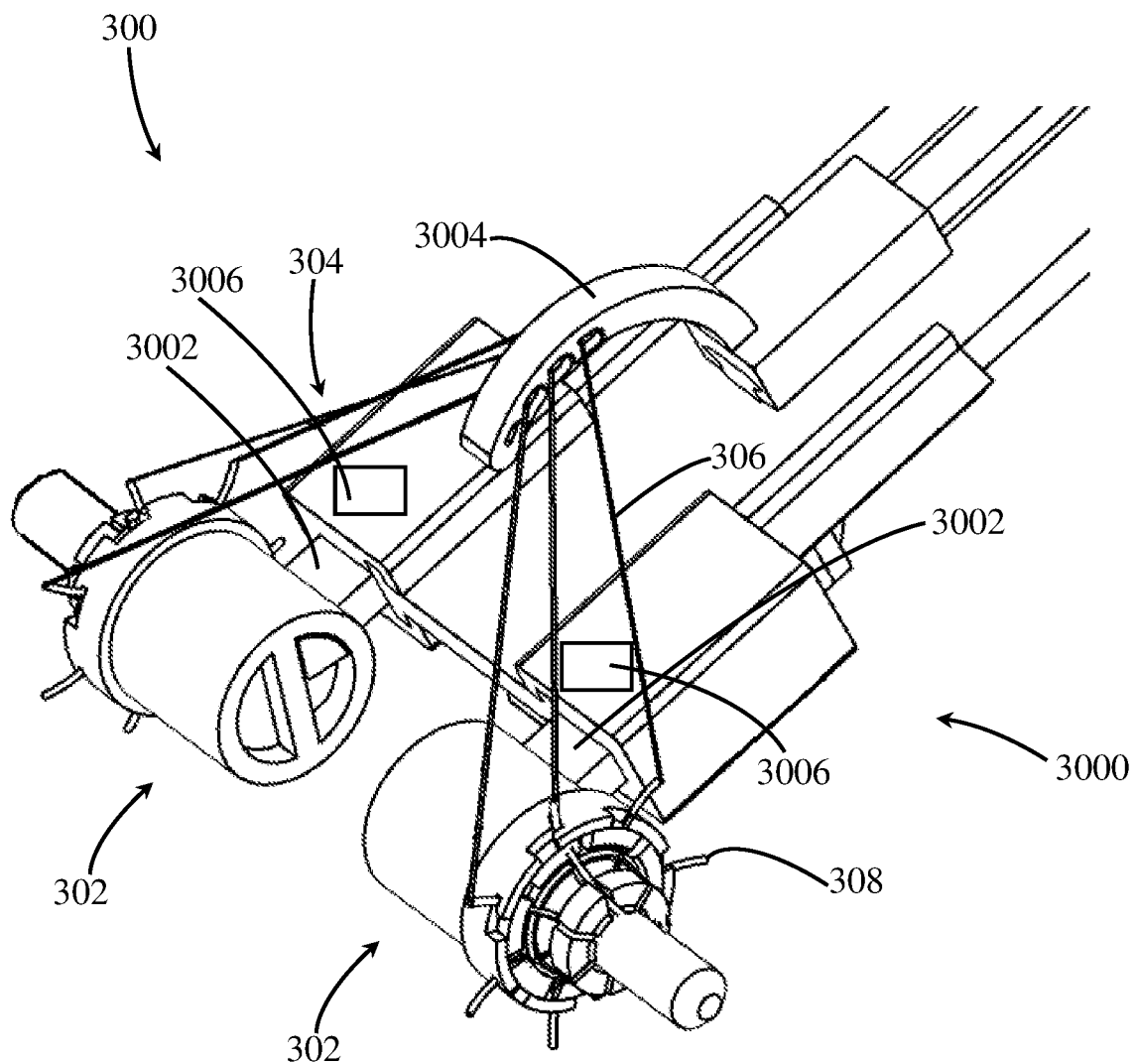
FIG. 5A shows a perspective view of an anastomosis arrangement comprising two separate coupling assemblies according to another embodiment of this disclosure, coupled to an actuator device for operating the anastomosis arrangement.
Figure 5B:
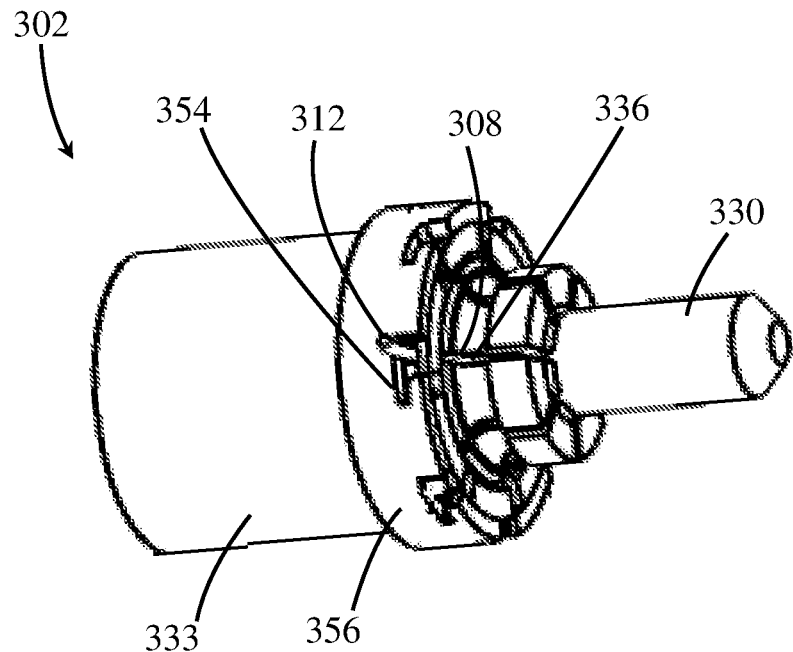
FIGS. 5B-5E are perspective views of a sequence of needle-extraction from a coupling assembly of the arrangement of FIG. 5A.

The arrangement 300 of FIG. 5A comprises a pair of coupling assemblies 302 linked by a plurality of suturing units 304, each suturing unit comprising a suturing thread 306 and a pair of curved suturing needles 308. Utilizing a pair of separate coupling assemblies provides higher degree of flexibility and adaptation to various conditions in the stump-coupling procedure, e.g. individual and independent manipulation of each of the coupling assemblies, positioning of the assemblies at different angles one with respect to the other, utilizing assemblies of different sizes, etc. In the exemplified embodiment, the coupling assemblies 302 are held together by an actuation device 3000. However, it is also contemplated that the coupling assemblies may be held together by an auxiliary unit (not shown) that has not actuation functionality, such as a bridge, a frame, a rigid, semi-flexible or flexible gig, etc.

The actuator device 3000 comprises two holding members 3002, each for holding one of the stump-coupling members 302 in a releasable manner, such that once deployed, the stump-coupling members may be detached from the actuation device for ease of removal from the operation site. In order to maintain the suturing threads 306 in at least a partially tensioned state during the stump-coupling procedure (e.g. to prevent entanglement of the threads during operation), the actuation device may comprise a thread-holder 3004 that is associated with the suturing threads in a releasable manner.

The actuator device may also comprise one or more magnetic elements 3006, which may be an integral part of the device, or removably attached to the device. Although in this specific example the magnetic element is shown as associated with a frame part of the device, it is but a mere example and the magnetic element can be associated with any other suitable part of the actuator device (or at times associated with an auxiliary frame holding the device). As noted, in the anastomosis procedure, the suturing needles 308 are manipulated to pierce and pass through the tissue, and after their full removal from the tissue may be magnetically held by the one or more magnetic elements 3006 until removal of the actuator device and/or anastomosis assembly. This allows the operator of the device to temporarily hold needles that are no longer in use during the procedure and reduce the risk of the suturing threads entanglement.

The operation of the coupling assemblies of this embodiment (shown in FIGS. 5B-5E) is similar to the operation of the assemblies in the embodiment described in FIGS. 1A-3C, and will thus be briefly described.

Shown in isolation in FIGS. 5B-5E is the sequence of operation of one coupling assembly 302 accommodating, for ease of exemplification, one suturing needle 308 (with the suturing thread being removed). The suturing needle 308 is accommodated within one of the channels in the set of open channels 336. In the first resting state of the needle, shown in FIGS. 5B-5C, the tip of the needle is accommodated within the channel 336. The rear end of the needle 312 is held by L-shaped opening 354 formed in the needles manipulation element 356, which is typically in the form of a sleeve element that is fitted over the body 333 of the coupling assembly in a manner that permits it to displace axially along and rotationally about longitudinal axis X'.

Figure 5C:
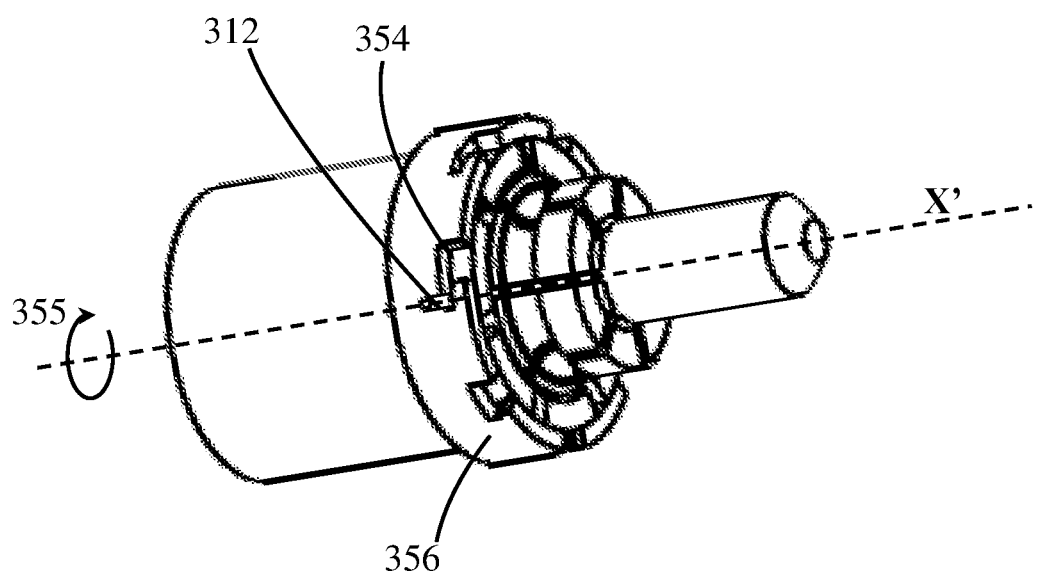
Figure 5D:
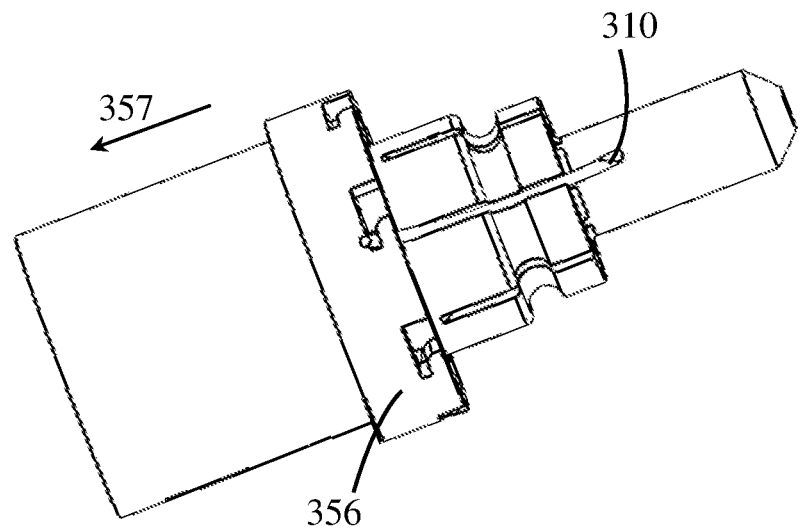
Figure 5E:
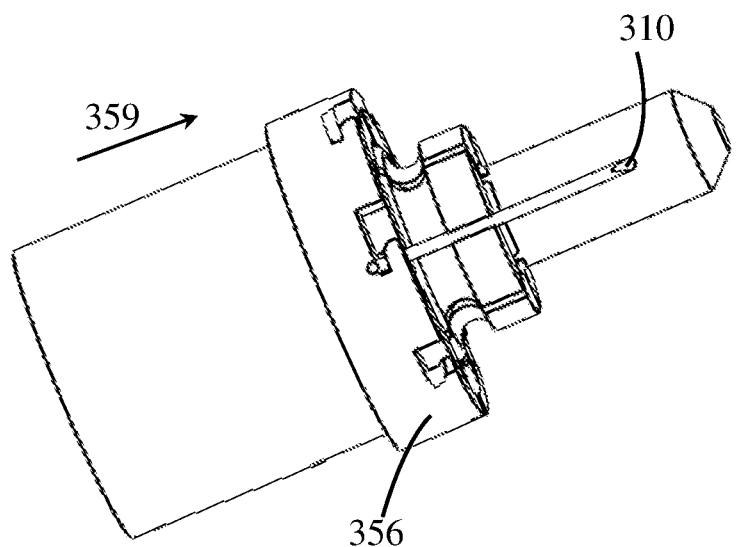

After the tissue stump has been fitted over the projection 330, the needles manipulation element 356 is rotated about the axis in the direction of arrow 355 in order to actuate the coupling assembly, thus locking the rear end 312 of the suturing needle 308 within opening 354 (as seen in FIG. 5C). Then, as seen in FIG. 5D, the needles manipulation element is axially displaced in the direction of arrow 357, causing the needle to pivot about the pivot point of channel 336 and transition into its the second rest state, in which the tip 310 of the needle is exposed and penetrates the walls of the stump (although not shown in this embodiment, the structure of channel 336 is similar to that of channel 136 better seen in FIG. 3A). In order to facilitate further penetration of the needle through the tissue stump and enable the practitioner to better grip the needle in order to pass it through the tissue, the needles manipulation element 356 may be axially displaced in the direction of arrow 359, into the position shown in FIG. 5E, thus pushing the needle's tip further through the tissue, providing better access to the needle's tip after its penetration to the tissue.

The invention claimed is:

1. Anastomosis arrangement for joining two stumps of a tubular organ, comprising:
   a coupling assembly and suturing units incorporated within the assembly;
   the coupling assembly comprises
      a pair of axially-symmetric coupling members defining two opposite axially-extending stump-coupling projections, each of said projections being configured for coupling with one of the stumps by pulling walls of the stump over external surface thereof to a suturing state in which the stump walls cover a stump-engaging portion thereof,
      two opposite sets of open channels, one in each of said stump-coupling projections arranged in an axially-symmetric manner about the axis, each of the open channels (i) extending between a rear channel end in said axially-symmetric coupling member and a front channel end in the stump-engaging portion of the stump-coupling projection to define a channel axis, (ii) being defined between side walls and a bottom wall that is configured with a pivot point in a mid-channel portion to define a front channel portion and a rear channel portion, and (iii) having a counterpart open channel in the opposite set that extends along the same channel axis in an opposite direction to the opposite stump-coupling portion, and comprises
      two needles manipulation elements, one in each axially-symmetric coupling member, each being axially displaceable between a front position nearer said stump-coupling projection and a rear, needle extraction position;
   each of the suturing units comprises
      a suturing thread and two curved suturing needles, each with a tipped front and a thread-coupled rear that is coupled to the thread,
      the suturing needles being each accommodated in one of the open channels, with one of the suturing needles of each suturing unit being accommodated in an open channel of one of said stump-coupling members and the other suturing needle of the suturing unit in the counterpart open channel in the other of said axially-symmetric coupling members,
      when at the front position, the front end of each needle being fully accommodated within the open channel proximal to the front channel end, a front portion of the needle resting against said front channel portion with a mid-portion of the needle resting against said pivot point, a rear portion of the needle does not rest against said rear channel portion, and the rear end of the needle extending out of the open channel proximal the rear channel end, and
      the rear end of the needle being coupled to the needles manipulation elements of the respective axially-symmetric coupling member such that upon the axial displacement thereof from the front position into the needle extraction position, the needles pivot about said pivot point, whereby the needles rear portion rests against said rear channel portion, the front portion of the needle does not rest against said front channel portion, and the tipped front is pivotally displaced out of said front channel end to pierce through the stump walls when in said suturing state.

2. The anastomosis arrangement of claim 1, wherein the axially-symmetric coupling members are connected to one another through a central connecting body.

3. The anastomosis arrangement of claim 1, wherein the axially-symmetric coupling members are separate members and held together by an auxiliary unit.

4. The anastomosis arrangement of claim 3, wherein the auxiliary unit is part of an assembly actuation device.

5. The anastomosis arrangement of claim 1, wherein the coupling assembly has a mirror symmetry about a plane of symmetry in between them.

6. The anastomosis arrangement of claim 1, wherein the stump-coupling projection has a circular cross-section.

7. The anastomosis arrangement of claim 1, wherein the stump-coupling projection is tapered.

8. The anastomosis arrangement of claim 1, wherein the needles manipulation element is formed as a sleeve over a portion of the stump-coupling member and axially slidable along and rotatable about an external surface of said portion.

9. The anastomosis arrangement of claim 1, wherein
each of the front and rear channel portions has a curvature that matches that of the suturing needle, and wherein
the axial displacement of the needles manipulation element into the needle extraction position causes the suturing needles to pivot about the pivot point between a first resting state in which a portion of the needle forward said mid-portion rests against the front channel portion and a second resting state in which a portion of the needle rearward said mid-portion rests against the rear channel portion.

10. The anastomosis arrangement as claimed in of claim 9, wherein the curvature of each of the rear channel portion and front channel portion is arched about, respective, rear curvature center and front curvature center, the rear curvature center being rearward offset vis-à-vis the front curvature center.

11. The anastomosis arrangement of claim 1, wherein the suturing needles have each a tip that is angled with respect to a trajectory defined by the needle's curvature in a general inward radial direction.

12. The anastomosis arrangement of claim 1, comprising a retaining element for retaining the suturing needles within the open channels.

13. The anastomosis arrangement of claim 12, wherein the retaining element is an elastic ring accommodated in a circumferential groove.

14. An actuator device configured for operating the anastomosis arrangement of claim 1, the actuator device comprising:
a handle and two arms each configured for coupling at a distal portion to one of the needles manipulation elements; and
an actuator configured for displacing the arms to cause each of distal portions to move towards the other to thereby axially displace the needles manipulation elements to the needle extraction position.

15. The actuator device of claim 14 for operating a pair of said axially-symmetric coupling members, comprising
two holding members, each one for holding one of the axially-symmetric coupling members in a releasable manner.

16. The actuator device of claim 14, comprising a thread-holder for releasable association with mid-portions of the suturing threads.

17. The actuator device of claim 14, comprising a selector permitting selected displacement of one of the arms.

18. The actuator device of claim 14, wherein the two arms have a coupling end that fits into a groove formed on the needles manipulation element's external face.

19. The actuator device of claim 14, comprising at least one magnet configured for magnetically holding the suturing needles after their extraction out of the stump walls.

* * * * *